United States Patent [19]

Salvo

[11] Patent Number: 4,778,389

[45] Date of Patent: Oct. 18, 1988

[54] STRESSLESS PIN OR POST

[76] Inventor: Christopher A. Salvo, 656 King St., Port Chester, N.Y. 10573

[21] Appl. No.: 860,493

[22] Filed: May 7, 1986

[51] Int. Cl.$^4$ ............................................. A61C 5/08
[52] U.S. Cl. ..................................... 433/221; 433/225
[58] Field of Search ............... 433/225, 221, 220, 174; 411/213

[56] References Cited

U.S. PATENT DOCUMENTS

| | | | |
|---|---|---|---|
| 758,750 | 5/1904 | Haldeman et al. | 433/221 |
| 868,964 | 10/1907 | Bultman | 433/221 |
| 1,018,803 | 2/1912 | Anderberg | 433/225 |
| 1,283,346 | 10/1918 | Spear | 411/213 |
| 3,434,209 | 1/1970 | Weissman | 433/215 |
| 3,874,081 | 4/1975 | Franklin et al. | 433/225 |
| 4,490,116 | 12/1984 | Deutsch et al. | 433/225 |

FOREIGN PATENT DOCUMENTS 0013918 7/1895 United Kingdom ............... 433/221

OTHER PUBLICATIONS

"A New Prefabricated Post and Core System, *The Journal of Prosthetic Dentistry*, vol. 52, pp. 631-634, 1984.
"Adaptation of a Prefabricated Post to Dentin", *The Journal of Prosthetic Dentistry*, vol. 53, No. 2, pp. 182-184, 1985.

Primary Examiner—Robert Peshock
Assistant Examiner—Adriene J. Lepiane
Attorney, Agent, or Firm—Lowe, Price, LeBlanc, Becker & Shur

[57] ABSTRACT

A stressless pin or post for dental preparation to seat in a predrilled hole or root canal without subjecting the tooth substance to lateral stress. The pin or post has a head, neck and shank and is an elongated member formed by crimping the midpoint of a bar, folding the bar in a predetermined configuration about the rings so that the pin or post consists of side-by-side sections joined only at the top of the head portion.

16 Claims, 2 Drawing Sheets

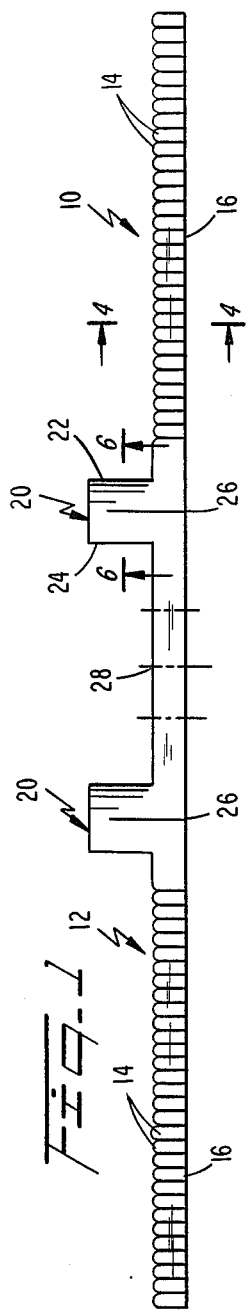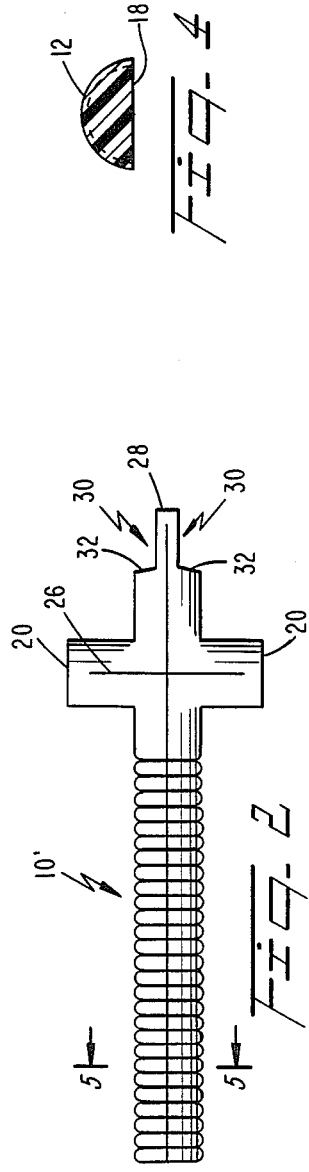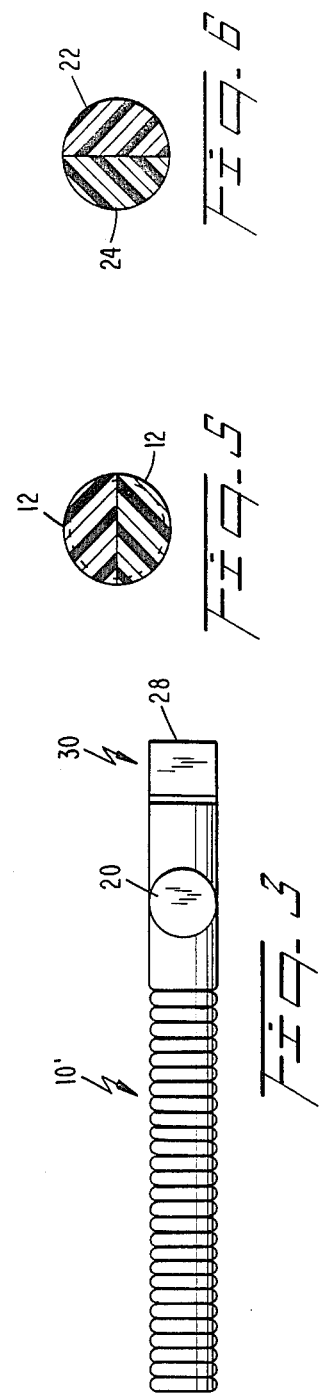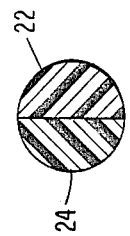

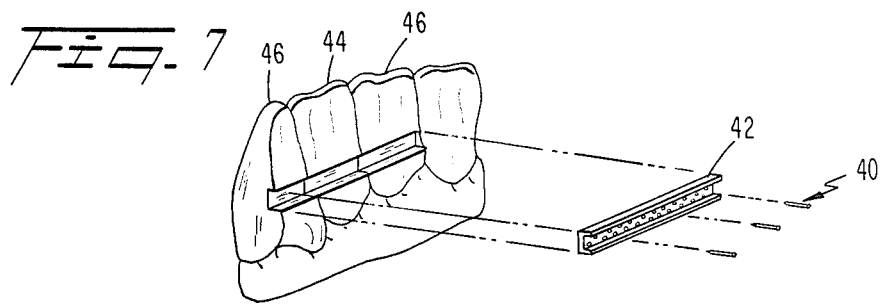
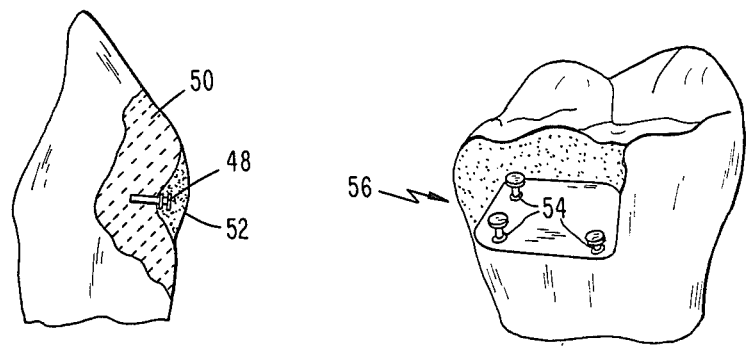
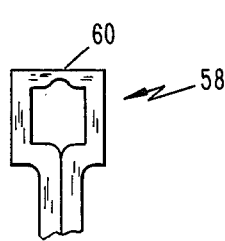 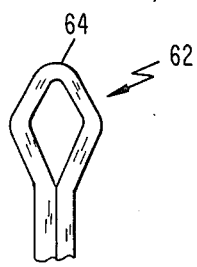 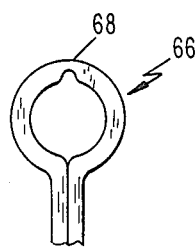
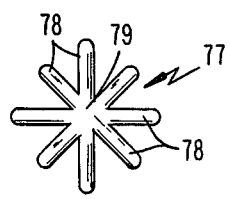 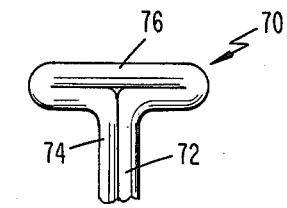 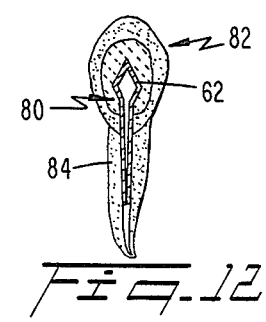

4,778,389

STRESSLESS PIN OR POST

FIELD OF THE INVENTION

This invention relates to a pin or post, intended to be inserted into a predrilled hole, which because of its design eliminates lateral stress against the walls thereof. The device of this invention is primarily adapted to the field of dentistry. Pin embodiments can be used, as will be subsequently explained for splints, orthodontic cleats, or to reinforce filling or crown core build-ups. Posts can be used in root canal therapy and core build-up using the post itself as the core center.

DESCRIPTION OF THE PRIOR ART

Pins have been used in dentistry for many years and have been designed in a wide variety of different types. Pins may be threaded textured, non-textured, ribbed, serrated, or the like. Pins are smaller and normally used in dentin or the second tooth layer. Posts, after root canal therapy, extend into the root with an exposed head for core build-up using the exposed head as the core center. It has been known that especially in root canal therapy, the insertion of a post places lateral stress on the root wall which can result in cracking or fracture.

In an effort to minimize lateral stress a post was designed having a split shank so that the lower portion thereof would compress as it is inserted into the root. The neck and head remain solid. See for example Musikant et al, "A New Prefabricated Post and Core System", Journal of Prosthetic Dentistry, V. 52, pp. 631-634, 1984; and Deutsch et al, "Retentive Properites of a New Post and Core System", Journal of Prosthetic Dentistry, V. 53, pp. 12-14, 1985

The split shank design, however, does not totally eliminate lateral stress in that as it is inserted in the tooth the unsplit portion acts as a fulcrum on the lever arm of the split shank whereby energy from the flexing of the shank members will be stored and translated into lateral pressure against the wall of the root.

SUMMARY OF THE INVENTION

It has been discovered, however, that such stresses from flexure of the split shank can be eliminated by providing a pin or post which is initially or optionally only joined at the very head end and which may have this joint severed as will be subsequently explained.

In one embodiment of this invention the pin or post may be formed as an elongatd member having for example a substantially hemispherical cross section. The rounded surface can be textured by etching, sand blasting, physically roughening or the like, or may form lateral ribs, knurls or screw like threads. The center point is then crimped and the opposed ends folded over until the flattened surfaces meet. A split pin is then provided joined only at the very head portion.

In one procedure for utilizing the pin of this invention the operator drills a hole suitable for the pin diameter, which is either the same diameter as the pin or very slightly larger. The pin is then inserted into the drilled hole and should exhibit virtually no compression along its unjoined length.

When the operator is satisfied that the pin and placement of the pin are roper the joined head section may be separated, after fitting and cementing or bonding, but before the cement or bond sets. This allows any stress developed in placement of the pin to dissipate. The separation also allows for vertical and rotational slippage in the unlikely event that there are residual stresses in those directions. Vertical slippage may be reduced also by the aforementioned texturizing of the outer surface.

In another embodiment, radial slits are further provided in the lateral wall of the pin perpendicular to the longitudinal axis.

It should be noted that the joined upper portion need not be separated. The externally located crimp or joint maximizes the lever arm effect at this joint.

When the pin is inserted, current cement or bonding techniques may be used, but if the joint is to be severed it should be done before the bonding material or cement is set.

As will be subsequently explained, the device of this invention may be made of metal or non metal, and may be in a wide variety of cross sectional shapes from the hemispherical above described to concave and convex. A variety of different head designs are also contemplated as will be subsequently described.

Accordingly, it is an object of this invention to provide a pin or post which may be inserted in a predrilled hole in a tooth without exhibiting stress on the tooth.

It is another object of this invention to provide a pin having a split terminating in an externally located joint at the uppermost portion of the head which can be severed if desired when the pin or post is used in a dental preparation.

It is a further object of this invention to provide a stressless pin or post having a fully split shank intended to eliminate lateral stress during placement consisting of two elongated portions joined only at the very uppermost portion so that during insertion, the pin will not cause lateral stress on the walls of a predrilled hole in a tooth.

These and other objects will become readily apparent with reference to the drawing and following, description wherein:

BRIEF DESCRIPTION OF THE DRAWINGS

FIG. 1 is a side view of an embodiment of the device of this invention prior to crimping and folding.

FIG. 2 is a side view of the device of FIG. 1 after crimping and folding.

FIG. 3 is a top view of the device of FIG. 2.

FIG. 4 is a cross sectional view taken along lines 4—4 of FIG. 1.

FIG. 5 is a cross sectional view taken along lines 5—5 of FIG. 2.

FIG. 6 is a cross sectional view taken along lines 6—6 of FIG. 1.

FIG. 7 is a exploded view of the pin device of this invention used in a dental splint.

FIG. 8 is a side view of an embodiment of this invention used for cavity retention.

FIG. 9 is a perspective view of a dental preparation utilizing pins of this invention prior to crown build-up.

FIG. 10A is a fragmentary view of an alternate embodiment.

FIG. 10B is a fragmentary view of another alternate embodiment.

FIG. 10C is a fragmentary view of still another alternate embodiment.

FIG. 10D is a fragmentary view of yet another alternate embodiment.

FIG. 11 is a top view of an laternal emboidment where multiple shanks are provided.

FIG. 12 is a cross sectional view illustrating a post device in a root canal.

DETAILED DESCRIPTION OF THE INVENTION

With attention to the drawings and to FIGS. 1-6 in particular, a preferred embodiment of this invention is an elongated member 10 which as shown in FIG. 4 may be hemispherical in cross section. In this embodiment the rounded upper surface 12 is shown as formed with ribs 14 extending along the shank portion 16. The undersurface 18 is flat as also shown in FIG. 4.

The upper surface 12 may in the alternative, mount screw threads, knurls or it may be merely roughened or etched. Obviously, the upper surface could also be smooth if desired. Further, the texurization can extend to include the head of the device.

In addition, this invention is not intended to be limited to a hemispherical cross section. For example, one half could be concave and the other half convex, or the cross section could be rectangular. Further, it coud be multi shanked producing a head as seen from the top end as in FIG. 11 and in cross section of the shank as seen in FIG. 12.

The device may be constructed of any conventional dental materials such as stainless steel, titanium, chrome cobalt alloy or the like, or in fact the device may be a non metal such as a resin.

In the embodiment pictured in FIGS. 1-3, raised portions 20 are provided which, as shown in FIG. 6, consist of opposed legs 22 and 24 which are divided by a slit 26. The device 10 has a midpoint 28. In manufacture, midpoint 28 is crimped to provide the folded device shown in FIGS. 2 and 3 having a reduced cross section in areas 30 due to the crimp. As shown in FIG. 1, the portions of pin 10 which extend to the right and the left of midpoint 28 are mere images of each other. Accordingly when the device is folded about its midpoint 28 to produce the pin or post 10' shown in FIGS. 2 and 3 the surface 18 of the right and left portions will meet and the pin 10' will be joined only at its very head portion at midpoint 28. The lateral slit 26 then will extend perpendicular to the longitudinal axis of the pin or post 10'. It is not necessary that both surfaces 16 produce a closed slit 26 in the longitudinal axis. Slight separation is required to absorb insertional stresses. Both legs are to be parallel to each other.

As will be obvious to those skilled in the art, the difference between a pin and a post is the length and width of the member. A pin is to extend into the dentin whereas a post is to extend into the root canal. A pin then by necessity must be very small. For example, in the device of this invention, the width of surface 18 may be 0.025 inches whereas the radius of the hemispherical portion 12 may be 0.0125 inches. Area 30 of the crimp may have a length of 0.060 inches extending from midpoint 28 toward face 32 which defines the extent of a reduced cross section due to crimping. The length of the pin 10' will depend upon the particular use to which the pin is to be placed.

The following are alternative sample specifications with dimensions in inches.

| | Size | | | | | | |
|---|---|---|---|---|---|---|---|
| | 0000 | 00 | 0 | 1 | 2 | 3 | 4 |
| HEAD LENGTH | .05 | .10 | .15 | .15 | .20 | .25 | .30 |
| SHAFT LENGTH | .30 | .30 | .30 | .34 | .40 | .45 | .53 |
| SHAFT DIAMETER | .027 | .030 | .040 | .045 | .055 | .065 | .075 |

NOTE:
Tolerances above are ±.005" with the exception of size 0000 where it is ±.002".
Metal to be used is stated elsewhere in this communication.

With reference to FIGS. 7, 8 and 9, conventional pins have found many applications in dentistry. With reference to FIG. 7, pins 40 may be used to secure a splint 42 whereby a loose tooth 44 is supported by abutment teeth 46. Such a splint is disclosed in my copending application Ser. No. 800,782, filed Nov. 22, 1985, now U.S. Pat. No. 4,735,571, issued Apr. 5, 1988, the disclosure of which is hereby incorporated by reference.

As shown in FIG. 8, a pin 48 may be placed in dentin 50 and used to secure a filling 52.

In addition, one or more pins 54 may be secured in a deep dental preparation 56 and thereby used to anchor a core build-up (not shown) in the conventional fashion. As will be apparent, this invention may include additional embodiments. With reference to FIG. 10A, there is disclosed an alternative head embodiment wherein the head 58 is rectangular or square with a crimp or minimum dimension shown at 60.

With reference to FIG. 10B, the head 62 is diamond shaped with the midpoint connector shown at 64.

With reference to FIG. 10C, the head 66 is shown as circular with a crimp 68 at the midpoint.

Finally, with reference to FIG. 10D, the head 70 may be flattened as for example if pressure were exerted at the midpoint 64 or 68 to compress the head. The only juncture between the two halves 72 and 74 remains at the midpoint 76.

FIG. 11 shows a multiple shank head 77 where multiple shanks 78 have a common juncture 79.

As will be obvious to those skilled in the art there are many other uses for pins and posts. As shown for example in FIG. 12 a post 80 is of particular use in providing an underdenture to support an overdenture 82 when the post 80 is seated in a root 84. A post 80 with a diamond shaped head 62 is shown as an illustration.

In each of the aforementioned instances, a hole is drilled which is the same diameter as the pin or post or slightly larger. When a conventional pin is inserted lateral stress will be placed upon the tooth structure or upon the root structure which can result in cracking. The pin or post of this invention is intended to "give" so that lateral stress can be released after insertion. This is achieved by the two halves which come together as the pin is inserted without a lever or coiling action as shown in FIG. 12. In the conventional split pin wherein only a portion of the shank is split with the neck and head solid, a coiling or spring action will result in stored energy and lateral stress as the split pin portions come together. By having only a minimal connection between the two halves at the tip of the head as in the device of this invention, either the tip of the head may be severed, or else as desired the pin may be inserted without severing the head. In either event, the resulting pin will be almost completely without the ability to exert lateral stress upon the tooth structure. The externally placed joint allows for longer lever arms and lowered lateral forces.

It is not intended to limit this invention to the specific head design shown herein. Furthermore, it is not intended to limit this invention to a particular type of material for construction.

The pin or post of this invention may be constructed from any metal or non metal acceptable in dentistry and may be coated or uncoated as described in my aforementioned copending patent application. As noted above, the outer surface of the pin or post of this invention may have screw threads, may be ribbed, may be roughened, or may be etched, or may be smooth without departing from the scope of this invention.

Typically in order to utilize the pin of this invention the operator will drill a hole about the same diameter as the pin or only slightly larger to ensure a snug fit. The length of the pin is then adjusted as desired to seat in the hole. If the hole is acceptable, typically the crimp in the head will be severed and the pin inserted. In the alternative, as noted above, there are applications when the severing of the crimp is not necessary. In any event, the pin is cemented or bonded, but the head should be severed for fullest stress reduction. If it is to be severed it should be severed before the bonding compound sets. Once the bonding compound is set, the dental procedure is completed.

In the embodiment of FIGS. 1-3, an optional slit is provided disposed perpendicular to the longitudinal axis of the pin. While one of such slits is shown, it will be obvious that more than one can be provided, or the slit may be unnecessary depending upon the application.

The invention may be embodied in other specific forms without departing from the spirit or essential characteristics thereto. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A virtually stressless pin or post for use in a dental preparation to seat in a hole in a tooth or a root canal without subjecting the tooth's substance to lateral stress comprising;
    an elongated member having a shank consisting of longitudinally extending sections having a predetermined cross-sectional configuration and a head consisting of a severable crimp having a cross-sectional dimension less than that of said sections, said sections extending through said head to the crimp so that said sections and extensions thereof are joined only at the crimp, the crimp being adapted to remain external to the tooth substance whereby the pin or post will exert only minimal stress to the internal parts of the tooth and if the crimp is severed any stress will be eliminated.

2. The pin or post of claim 17 wherein said sections are mirror images of each other.

3. The pin or post of claim 2 wherein said member has a hemispherical cross sectional configuration and the flat surfaces of said sections abut each other.

4. The pin or post of claim 1 wherein the head is folded in the configuration of a rectangle.

5. The pin or post of claim 1 wherein the head is folded in the configuration of a circle.

6. The pin or post of claim 1 wherein the head is folded in the configuration of a diamond.

7. The pin or post of claim 1 wherein the head is flattened against the shank.

8. The pin or post of claim 1 wherein the section extensions extend radially from said crimp and are folded in a predetermined configuration.

9. The pin or post of claim 1 wherein the member defines at least one lateral extension perpendicular to the longitudinal axis thereof which extension defines an internal, stress reducing spacer split contained in a plane disposed perpendicular to the longitudinal axis of said member.

10. The pin or post of claim 9 wherein a plurality of lateral extensions are provided, each defining a stress reducing split.

11. The pin or post of claim 9 wherein the lateral extension is adapted to be disposed externally to the tooth substance in the head thereof.

12. The pin or post of claim 1 wherein the external surface of the shank is roughened.

13. The pin or post of claim 1 wherein the external surface of the shank is ribbed.

14. The pin or post of claim 1 wherein the external surface is roughened.

15. The pin or post of claim 1 wherein the external surface of the shank is etched.

16. The pin or post of claim 1 wherein the external surface of the shank is coated with a dental bonding agent.

* * * * *